(12) United States Patent
Vallon et al.

(10) Patent No.: US 9,255,858 B2
(45) Date of Patent: Feb. 9, 2016

(54) METHOD FOR MEASURING FIBER CUTTING FORCE

(75) Inventors: Mark David Vallon, Framingham, MA (US); Matthias Gester, Farnborough (GB)

(73) Assignee: The Gillette Company, Boston, MA (US)

( * ) Notice: Subject to any disclaimer, the term of this patent is extended or adjusted under 35 U.S.C. 154(b) by 837 days.

(21) Appl. No.: 13/027,478

(22) Filed: Feb. 15, 2011

(65) Prior Publication Data

US 2011/0214493 A1    Sep. 8, 2011

Related U.S. Application Data

(60) Provisional application No. 61/309,913, filed on Mar. 3, 2010.

(51) Int. Cl.
| | | |
|---|---|---|
| *G01N 19/02* | (2006.01) | |
| *G01L 5/00* | (2006.01) | |
| *G01N 3/58* | (2006.01) | |
| *B23Q 17/09* | (2006.01) | |
| *B26B 21/40* | (2006.01) | |

(52) U.S. Cl.
CPC ............. *G01L 5/0076* (2013.01); *B26B 21/40* (2013.01); *B26B 21/4087* (2013.01); *G01N 3/58* (2013.01); *B23Q 17/09* (2013.01); *B26B 21/4081* (2013.01); *B26B 21/4093* (2013.01); *G01L 5/0028* (2013.01)

(58) Field of Classification Search
CPC .. G01N 3/58; B26B 21/4081; B26B 21/4087; B26B 21/4093; G01L 2/0028; B23Q 17/09
USPC ............................................ 73/104–105, 159
See application file for complete search history.

(56) References Cited

U.S. PATENT DOCUMENTS

| | | | | |
|---|---|---|---|---|
| 2,469,385 | A | | 5/1949 | Hallock |
| 4,178,797 | A | * | 12/1979 | Kozlowski, Jr. ............... 73/104 |
| 4,528,843 | A | * | 7/1985 | Juranitch ..................... 73/104 |
| 5,181,416 | A | * | 1/1993 | Evans ......................... 73/104 |
| 5,211,060 | A | | 5/1993 | O'Brien et al. |
| 5,379,633 | A | * | 1/1995 | Flisram et al. ................ 73/104 |
| 5,571,956 | A | * | 11/1996 | Sargent ....................... 73/104 |
| 7,293,451 | B2 | * | 11/2007 | Dowd .......................... 73/105 |
| 7,344,498 | B1 | | 3/2008 | Doughty et al. |

(Continued)

FOREIGN PATENT DOCUMENTS

FR    2 749 793    12/1997

OTHER PUBLICATIONS

PCT Intetnational Search Report with Written Opinion in corresponding Int'l appln. PCT/US2011/026653 dated May 31, 2011.

(Continued)

*Primary Examiner* — Lisa Caputo
*Assistant Examiner* — Jonathan Dunlap
(74) *Attorney, Agent, or Firm* — Joanne N. Pappas; Kevin C. Johnson; Steven W. Miller

(57) ABSTRACT

A method for measuring the cutting force on a fiber. The method includes the steps of: providing a blade having an edge; providing a fiber mount for holding the fiber; providing at least one sensor connected to the fiber mount; moving the blade toward the fiber and cutting the fiber; and measuring the cutting force on the fiber with the at least one sensor.

16 Claims, 2 Drawing Sheets

(56) References Cited

U.S. PATENT DOCUMENTS

| | | | |
|---|---|---|---|
| 8,047,069 B2 * | 11/2011 | Coulter et al. | 73/159 |
| 2006/0201237 A1 | 9/2006 | Dowd | |
| 2010/0300195 A1 * | 12/2010 | Coulter et al. | 73/159 |
| 2012/0123444 A1 * | 5/2012 | Verhagen et al. | A61B 18/20 606/133 |

OTHER PUBLICATIONS

Thozhur, S. M., Crocombe, A. D., Smith, P.A., Cowley, K., Mullier, M. "Cutting Characteristics of Beard Hair." *Journal of Material Science* 42:8725-8737 (Jan. 4, 2007).

Thozhur, S. M., Crocombe, A. D., Smith, P.A., Cowley, K., Mullier, M. "Structural Characteristics and Mechanical Behaviour of Beard Hair." *Journal of Material Science* 41 1109-1121 (Feb. 4, 2006).

* cited by examiner

METHOD FOR MEASURING FIBER CUTTING FORCE

CROSS REFERENCE TO RELATED APPLICATIONS

This application claims the benefit of U.S. Provisional Application No. 61/309,913, filed Mar. 3, 2010.

FIELD OF THE INVENTION

The present invention relates to a method for measuring the cutting force on a fiber, and more particularly, to a method for measuring the cutting force exerted by a blade on a fiber such as a hair.

BACKGROUND OF THE INVENTION

In general, many techniques have been used over the years to measure the cutting forces of a blade cutting different materials. For example, the wool felt cutter test measures the force on a blade as the blade cuts through wool felt. This method has worked satisfactorily over the previous years for measuring the force on the blade as the blade cuts through the wool felt. However, the wool felt cutter test is only able to differentiate between blades when the differences in the cutting force exerted on the blades have relatively high measurable differences.

Another drawback with the wool felt cutter test is that it measures the force on the blade. The blade is held in a stationary position with a sensor attached to the blade. The wool felt is then moved across the blade edge to be cut. The sensor detects the force exerted on the blade as the blade edge cuts the wool felt.

In the wool felt cutter test, it is not known how many fibers are actually present in the wool felt. Furthermore, when the test is conducted it is not known how many fibers are actually cut by the blade and how far from the base the fibers have been cut.

Furthermore, in the wool fell cutter, blades have to remain static and dynamic cutting action like a sawing motion cannot be studied.

There is a need to provide a method for measuring the cutting force experienced by the fiber itself as the fiber is cut by a blade.

There is a need to provide a method for measuring the cutting force experienced by a hair as the hair is cut by a blade. Such a method would provide a more accurate measurement of the actual cutting force that is exerted on the hair by the blade during shaving.

There is a need to provide a method for measuring the cutting forces with a relatively high degree of sensitivity in order to determine the differences in the cutting forces between different blades.

There is a need to provide a method for measuring the cutting forces on different types of fibers.

There is a need to provide a method for measuring the cutting forces on hairs having different physiology and/or different chemical or mechanical treatment prior to cutting.

There is a need to provide a method for measuring the cutting force on hairs when the blades oscillate in specific direction, e.g. create a sawing, chopping or scraping movement, or with blades that are heated or electrically charged.

SUMMARY OF THE INVENTION

The present invention provides a method for measuring the cutting force on a fiber. A blade having an edge is provided. A fiber mount for holding the fiber is provided. At least one sensor connected to the fiber mount is provided. The blade is moved toward the fiber and cuts the fiber. The cutting force on the fiber is measured with the sensor.

The fiber mount may comprise a fiber outlet. The fiber outlet may have a shape selected from the group of circular, square, triangular, oval, and rectangular. The fiber may extend from the outlet by a distance from about 0.01 mm to about 2.0 mm prior to being cut.

The fiber mount may comprise a trough which is able to hold a fluid. The fluid may alter or modify the chemical or mechanical properties of the fiber prior to cutting. The fluid may be water.

A blade mount to hold the blade may be provided. The blade mount can be moved to cut the fiber with different portions of the edge. The blade mount may be dimensioned to hold at least two blades. The blade mount can hold the blade at different angles with respect to the fiber mount.

The apparatus may comprise multiple sensors. The multiple sensors measure cutting forces in multiple directions.

The apparatus may contain actuators on the blade mount to create additional blade motion or may contain electrically connections to heat or electrically charge the blade.

BRIEF DESCRIPTION OF THE DRAWINGS

While the specification concludes with claims particularly pointing out and distinctly claiming the subject matter that is regarded as the present invention, it is believed that the invention will be more fully understood from the following description taken in conjunction with the accompanying drawings.

DETAILED DESCRIPTION OF THE INVENTION

Figure 1:
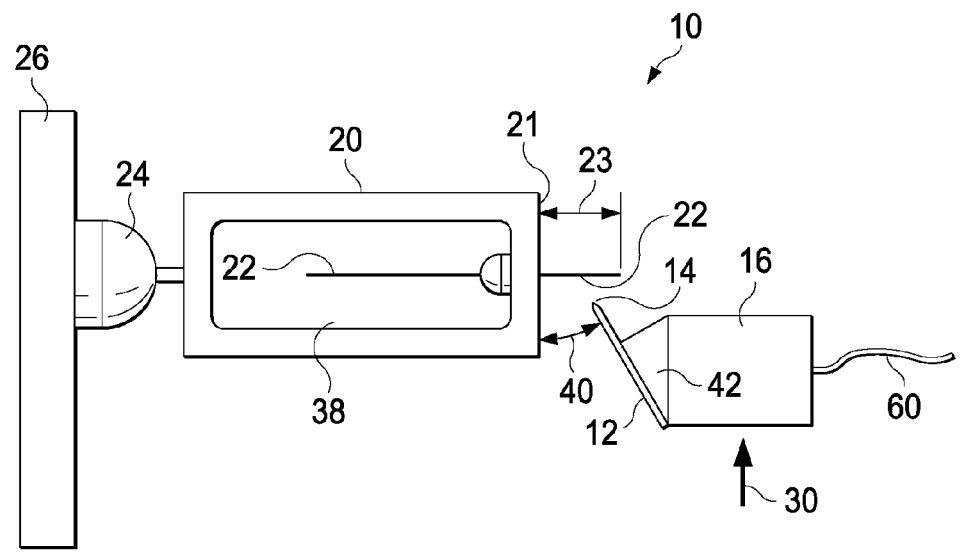
FIG. 1 is a top plan view of a fiber cutting apparatus of the present invention.

A cutting apparatus 10 for measuring the cutting force on a fiber is shown in FIG. 1. The cutting apparatus 10 includes a blade 12 having an edge 14. The blade 12 may be supported or held by a blade mount 16. The cutting apparatus 10 includes a fiber mount 20 for holding said fiber 22. A sensor 24 is connected to the fiber mount 20. The sensor 24 is shown mounted to a fixture 26. During operation of apparatus 10, blade mount 16 moves linearly in direction 30 towards fiber 22 moving blade 12 towards fiber 22 until blade 12 cuts fiber 22. As blade 12 cuts fiber 22 sensors 24 measures the cutting force exerted by blade 12 on fiber 22.

The fiber mount 20 may include a trough 38. Trough 38 may be configured to hold water or other fluids and/or liquids. For example, trough 38 may hold shave creams and shave preps or any other chemistry to modify the hair properties prior to cutting. Water may be added to trough 38 to hydrate the fiber 22 prior to being cut by blade 12. The trough may also contain another fluid including detergents, dye, salt solution, wax, a micro- or nano-particle suspension or others that modify and/or alter the chemical or mechanical properties of the fiber prior to cutting.

Different fibers may be cut with apparatus 10. Examples of such fibers include but are not limited to head hair, beard hair, leg hair, nylon, thread, yarn, wool, synthetic fibers, natural fibers, monofilament fibers, bi-component or multi-component fibers, etc. Fibers of different diameters or cross sections may also be cut with apparatus 10.

The blade mount 16 can be adjusted to hold blade 12 at different angles 40 with respect to fiber mount 20. For example, blade mount 16 may include a blade support 42. Blade supports 42 having different shapes may be used to position blade 12 at different angles 40 with respect to fiber mount 20.

The blade mount 16 may be connected to a power source via power supply cable 60 to provide power to blade mount 16. With the available power the blade mount 16 may be equipped to heat the blade 12. The blade mount 16 may be equipped to electrically charge blade 12. The blade mount 16 may oscillate in a specific direction to create a sawing, chopping or scraping movement by blade 12 with respect to fiber 22.

The fiber 22 may extend from the fiber mount 20 by a distance 23 of from about 0.01 mm, 0.05 mm, 0.1 mm, 0.2 mm, 0.3 mm, 0.4 mm and 0.5 mm to about 1.0 mm, 2.0 mm, 3.0 mm, 4.0 mm and 5.0 mm Preferably the fiber 22 extends from the fiber mount 20 by a distance 23 of from about 0.5 mm to about 2.0 mm.

The blade 12 may be positioned relative to the fiber mount to cut the fiber 22 at a distance of from about 0.01 mm, 0.5 mm, 0.1 mm to about 0.2 mm, 0.3 mm, 0.4 mm and 0.5 mm.

Figure 2:
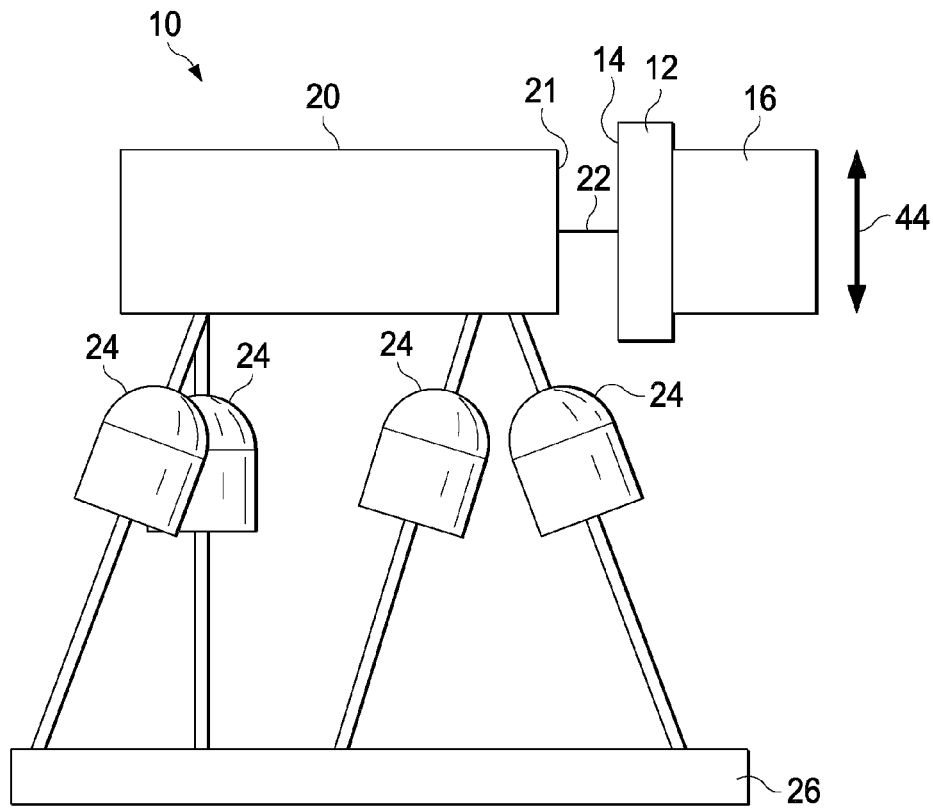
FIG. 2 is a side view of another fiber cutting apparatus of the present invention.

Another cutting apparatus 10 for measuring the cutting force on a fiber is shown in FIG. 2. The cutting apparatus 10 includes a blade 12 having an edge 14. The blade 12 may be supported or held by a blade mount 16. The cutting apparatus 10 includes a fiber mount 20 for holding said fiber 22. Pluralities of sensors 24 are connected to the fiber mount 20. The sensors 24 are shown mounted to a fixture 26. Apparatus 10 is shown with four sensors 24. Apparatus may have any number of sensors. For example, apparatus 10 may have one, two, three, four, or more sensors 24. Sensors 24 measure cutting forces in multiple directions different from one another. During operation of apparatus 10, blade mount 16 moves linearly towards fiber 22 moving blade 12 towards fiber 22 until blade 12 cuts fiber 22. As blade 12 cuts fiber 22 sensors 24 measure the cutting force exerted by blade 12 on fibers 22.

The fiber mount 20 may include a trough such as trough 38 shown in FIG. 1. The blade mount 16 can be adjusted to hold blade 12 at different angles with respect to fiber mount 20 as discussed with respect to FIG. 1.

Figure 3:
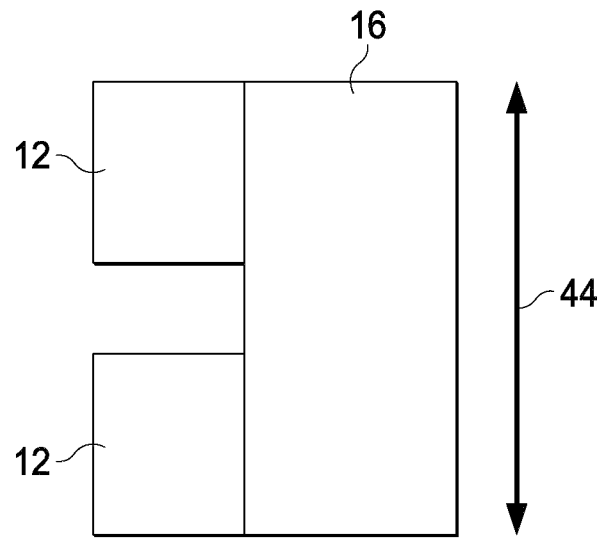
FIG. 3 is a side view of a blade mount of the present invention holding two blades.

The blade mount 16 can be moved in a direction indicated by arrow 44 to cut the fiber 22 with different portions of the blade 14. Referring now to FIG. 3, blade mount 16 is shown holding two blades 12. Blade mount 16 may hold more than two blades 12. For example blade mount 16 may hold three, four, or more blades 12. Blade mount 16 can be moved in a direction indicated by arrow 44 to first cut a fiber with one blade and then cut a fiber with the other blade.

Figure 4:
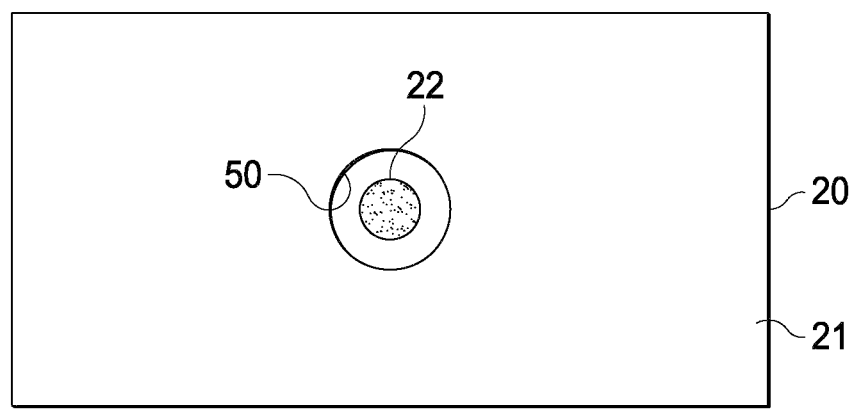
FIG. 4 is a front view of a fiber mount of the present invention.

Referring now to FIGS. 1, 2 and 4, fiber mount 20 has a front face 21 from which fiber 22 extends. Front face 21 has a fiber outlet 50 through which fiber 22 are fed. In FIG. 4, fiber outlet 50 is shown to have a circular shape. Other shapes such as square, triangular, oval, and rectangular may be used for fiber outlet 50.

The fiber 22 may be fed through fiber outlet 50 either manually or automatically. Preferably, the fiber 22 is held by clamps, rollers, or other devices while the fiber 22 is cut by blade 12. The fiber may be clamped rigidly. Alternatively the fiber may be held between two deformable pads, such as rubber or elastic pads, to simulate the way a hair is embedded in skin tissue.

The fiber 22 is shown to extend from fiber mount 20 substantially perpendicular to front face 21. Fiber 22 may be positioned to extend from fiber mount 20 at various angles with respect to front face 21.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for measuring the cutting force on a fiber, said method comprising the steps of:
  a. providing a blade having an edge;
  b. providing a fiber mount for holding said fiber;
  c. providing at least one sensor connected to said fiber mount;
  d. moving said blade toward said fiber and cutting said fiber; and
  e. measuring the cutting force on said fiber with said sensor.

2. The method of claim 1 wherein said fiber mount comprises a fiber outlet.

3. The method of claim 2, wherein said fiber outlet has a shape selected from the group of circular, square, triangular, oval, and rectangular.

4. The method of claim 2, wherein said fiber extends from said outlet by a distance from about 0.01 mm to about 2.0 mm prior to being cut.

5. The method of claim 1 wherein said fiber mount comprises a trough.

6. The method of claim 5, wherein said trough is able to hold a fluid.

7. The method of claim 6, wherein said fluid is able to modify chemical or mechanical properties of said fiber.

8. The method of claim 6, wherein said fluid is water.

9. The method of claim 1, further comprising the step of providing a blade mount to hold said blade.

10. The method of claim 9, wherein said blade mount can be moved to cut said fiber with different portions of said edge.

11. The method of claim 9, wherein said blade mount holds at least two blades.

12. The method of claim 9, wherein said blade mount can hold said blade at different angles with respect to said fiber mount.

13. The method of claim 9, wherein said blade mount heats said blade.

14. The method of claim 9, wherein said blade mount provides an electrical charge to said blade.

15. The method of claim 1, wherein said apparatus comprises multiple sensors.

16. The method of claim 15, wherein said sensors measure cutting forces in multiple directions.

\* \* \* \* \*